US009880147B2

(12) United States Patent
Astarita et al.

(10) Patent No.: US 9,880,147 B2
(45) Date of Patent: Jan. 30, 2018

(54) FREE AND TOTAL FATTY ACID DETERMINATION USING DESORPTION IONIZATION—MASS SPECTROMETRY

(71) Applicant: Waters Technologies Corporation, Milford, MA (US)

(72) Inventors: Giuseppe Astarita, Hopkinton, MA (US); Donald Mason, Haverhill, MA (US); Michael P. Balogh, Rehoboth, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 15/165,355

(22) Filed: May 26, 2016

(65) Prior Publication Data

US 2016/0349233 A1 Dec. 1, 2016

Related U.S. Application Data

(60) Provisional application No. 62/168,214, filed on May 29, 2015.

(51) Int. Cl.
*H01J 49/26* (2006.01)
*G01N 33/483* (2006.01)
(Continued)

(52) U.S. Cl.
CPC ......... *G01N 33/4833* (2013.01); *G01N 33/92* (2013.01); *H01J 49/005* (2013.01);
(Continued)

(58) Field of Classification Search
CPC . G01N 33/4833; G01N 33/92; H01J 49/0027; H01J 49/0045; H01J 49/005; H01J 49/165; H01J 49/10
(Continued)

(56) References Cited

U.S. PATENT DOCUMENTS

2010/0200742 A1* 8/2010 Schultz ............... H01J 49/0045
250/252.1
2012/0156712 A1 6/2012 Takats
(Continued)

FOREIGN PATENT DOCUMENTS

| WO | 2004087737 A2 | 10/2004 |
|---|---|---|
| WO | 2010031588 A2 | 3/2010 |
| WO | 2012037365 A1 | 3/2012 |

OTHER PUBLICATIONS

Astarita, Giuseppe, et al., "A Protective Lipidomic Biosignature Associated with a Balanced Omega-6/Omega-3 Ratio in fat-1 Transgenic Mice", PLOS One, Apr. 2014, vol. 9, Issue 4, pp. 1-11.
(Continued)

*Primary Examiner* — Nicole Ippolito
(74) *Attorney, Agent, or Firm* — Womble Bond Dickinson (US) LLP; Deborah M. Vernon; Rebecca N. Barnes

(57) ABSTRACT

The present disclosure relates to methods and apparatus for the determination of free fatty acids and total fatty acids in a sample. In particular, the present disclosure relates to the determination of free fatty acids and total fatty acids using desorption ionization-mass spectrometry. The methods and apparatus can include either in-source or post-ionization fragmentation of fatty acid containing compounds.

12 Claims, 9 Drawing Sheets

(51) Int. Cl.
- *H01J 49/00* (2006.01)
- *H01J 49/16* (2006.01)
- *G01N 33/92* (2006.01)
- *H01J 49/10* (2006.01)

(52) U.S. Cl.
CPC ...... *H01J 49/0027* (2013.01); *H01J 49/0045* (2013.01); *H01J 49/165* (2013.01); *H01J 49/10* (2013.01)

(58) Field of Classification Search
USPC ...... 250/281, 282, 283, 288; 702/22, 23, 26, 702/27
See application file for complete search history.

(56) References Cited

U.S. PATENT DOCUMENTS

| 2013/0299688 A1 | 11/2013 | Balogh et al. |
| 2015/0170893 A1 | 6/2015 | Shion et al. |

OTHER PUBLICATIONS

HS-Omega Index, Clinical Applications, 2011, pp. 1-23.

Astarita, Giuseppe, et al., "An Emerging Role for Metabolomics in Nutrition Science", Journal of Nutrigenetics and Nutrigenomics, 2013, vol. 6, pp. 179-198.

Murphy, M. Paul., et al., "Changes in Cognition and Amyloid-B Processing with Long Term Cholesterol Reduction using Atorvastatin in Aged Dogs", Journal of Alzheimer's Disease, 2010, vol. 22, pp. 135-150.

Harris, William S., "Omega-3 Fatty Acids and Cardiovascular Disease: A Case for Omega-3 Index as a New Risk Factor", Pharmacological Research, 2007, vol. 55, pp. 217-223.

Astarita, Giuseppe, et al., "Towards a Whole-Body Systems [Multi-Organ] Lipodomics in Alzheimer's Disease", Prostaglandins, Leukotrienes and Essential Fatty Acids, Nov. 2011, vol. 85, No. 5, pp. 1-7.

Laiakis, Evagelia C., et al., "Metabolic Phenotyping Reveals a Lipid Mediator Response to Ionizing Radiation", Journal of Proteome Research, pp. 1-44.

Harris William S., et al., "The Omega-3 Index: A New Risk Factor for Death from Coronary Heart Disease", Preventive Medicine, 2004, vol. 39, pp. 212-220.

Harris, William S., "The Omega-3 Index as a Risk Factor for Coronary Heart Disease", The American Journal of Clinical Nutrition, 2008, vol. 87, pp. 1997S-2002S.

Astarita, Giuseppe, et al., "An Emerging Role for Metabolomics in Nutrition Science", Journal of Nutrigenetics and Nutrigenomics, 2013, vol. 6, pp. 173-198.

Astarita, Giuseppe, et al., "Towards a Whole-Body Systems [Multi-Organ] Lipidomics in Alzheimer's Disease", Prostaglandins, Leukotrienes and Essential Fatty Acids, Nov. 2011, vol. 85, No. 5, pp. 1-7.

* cited by examiner

FIG. 1
Fatty Acids: the Lipids Backbone
Fatty acyl: fatty acid (FFA)
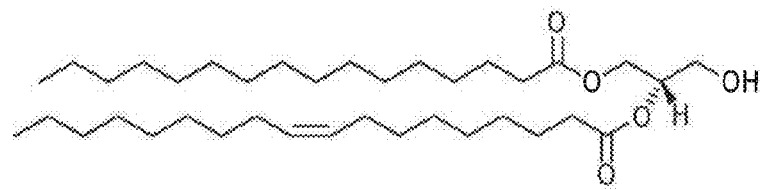
Glycerolipids: diacylglycerol (DG)
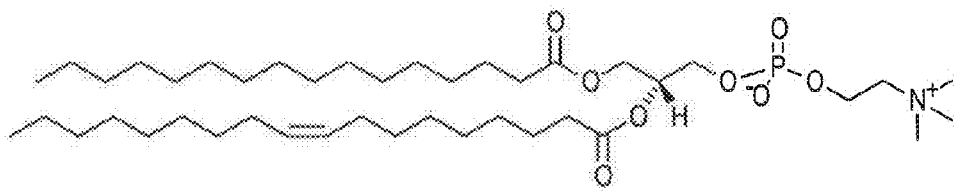
Glycerophospholipids: phosphatidylcholine (PC)
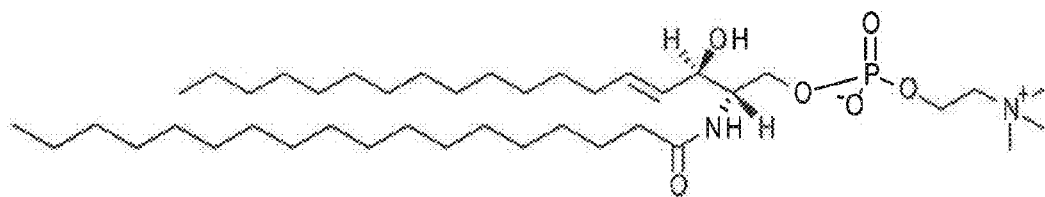
Sphingolipids: sphingomyelin (SM)

Complex lipids break down into simpler structures: fatty acids

No fragments

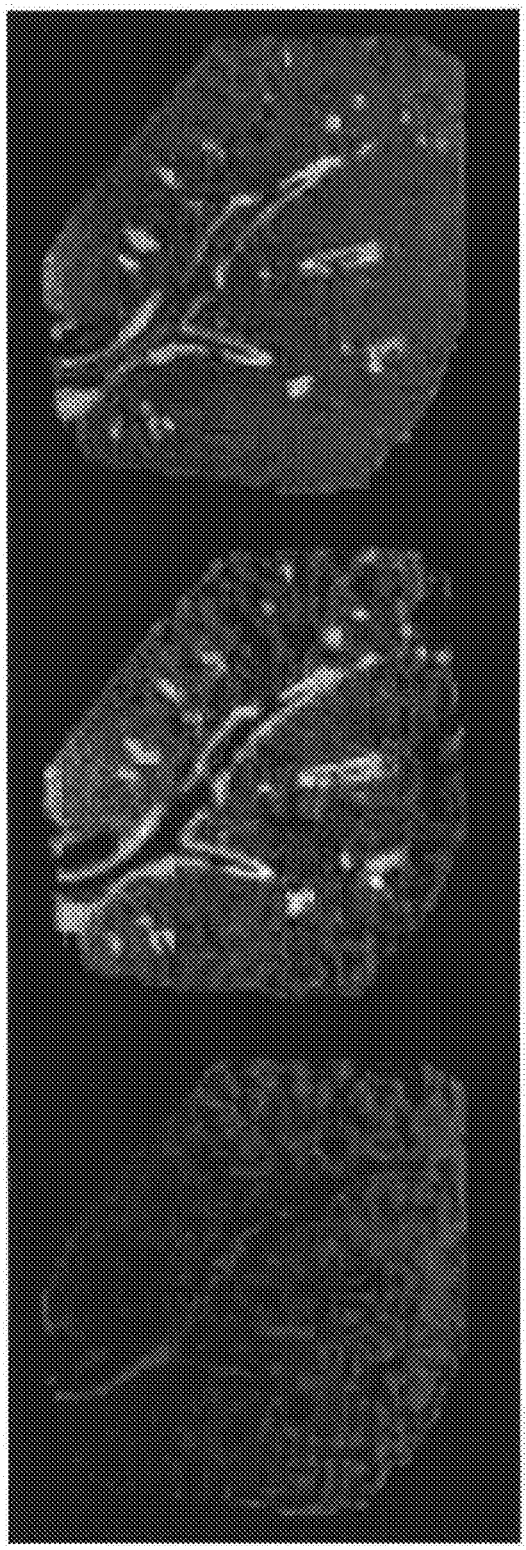
FIG. 8  Fatty Acid Imaging
PC 38:4 = FA 20:4 + FA 18:0; isomers = FA 20:3 + FA 18:1 etc...

FREE AND TOTAL FATTY ACID DETERMINATION USING DESORPTION IONIZATION—MASS SPECTROMETRY

CROSS-REFERENCE TO RELATED APPLICATIONS

This application claims the benefit of and priority to U.S. Provisional Patent Application No. 62/168,214, filed on May 29, 2015, the entire contents of which is incorporated herein by reference.

FIELD OF THE INVENTION

The present disclosure relates generally to methods and apparatus for the determination of free fatty acids and total fatty acids in a sample. In particular, the present disclosure relates to the determination of free fatty acids and total fatty acids using desorption ionization-mass spectrometry. The methods and apparatus can include either in-source or post-ionization fragmentation of fatty acid containing compounds.

BACKGROUND OF THE INVENTION

Fatty acids can be present in samples both in unesterified (free) and esterified forms (e.g., as glycerolipids, glycerophospholipids, sterol lipids and sphingolipids). The fatty acid content in a sample can be underestimated using analytical test methods that only test for free fatty acids. In some situations, the total fatty acid content can be more representative of the overall status of a biological system or the nutritional value of a food.

Current test methods for determining fatty acids require laborious and time-consuming procedures which negatively affect the sensitivity of detection. For example, gas chromatography-mass spectrometry (GC-MS) has been traditionally the technique of choice. Analysis by GC-MS, however, requires a multi-step procedure for the hydrolysis and derivatization of the fatty acids to fatty acid methyl esters, and a chromatographic separation. Alternatively, liquid chromatography-tandem mass spectrometry (LC-MS) has been used and allows for the direct measurement of both free and esterified fatty acids without the need for hydrolysis or derivatization. Yet, LC-MS still requires the labor intensive and time consuming chromatographic separation step. Supercritical fluid chromatography-mass spectrometry and other similar techniques has also been used, but these techniques suffer from the same requirement. Furthermore, any detailed spatial distribution of these species on a sample surface is unavailable using traditional sample preparation and extraction protocols.

The present disclosure relates to methods and apparatus for determining both free and total fatty acids which are less time consuming and resource intensive.

SUMMARY OF THE INVENTION

In general, the present disclosure relates to methods and apparatus for the determination and simultaneous profiling of free fatty acids and total fatty acids in a sample. In some embodiments, the determination of free fatty acids and total fatty acids can be performed using desorption ionization coupled with an ion source or in-cell fragmentation. The energy of the excitation source (e.g., laser, ions, heat) associated with the desorption ionization source (e.g., matrix assisted laser desorption ionization, rapid evaporative ionization mass spectrometry, direct analysis in real time) can be increased to induce fragmentation of a complex compound containing fatty acids (e.g., a complex lipid species) into its basic components (e.g., fatty acids) that can be detected using mass spectrometry in negative ionization mode. Alternatively, the energy can be increased in a collision cell located post-ionization source to induce fragmentation. The method and the apparatus of the present disclosure can be used for both direct analysis, real-time mass spectrometry applications and for mass spectrometry imaging. The total fatty acids distribution in a sample, e.g., tissue, can be generated.

The method and apparatus of the present disclosure provides numerous advantages. For example, the methods and apparatus for determining both free and total fatty acids are less time consuming and resource intensive then conventional methods. As a result, the methods and apparatus can be used to proactively analyze, monitor, and treat subjects. In addition, the present technology allows for in situ studies of samples (e.g., tissue). For example, imaging techniques can be used to map and track the distribution of fatty acids in the sample.

BRIEF DESCRIPTION OF THE DRAWINGS

The foregoing and other advantages provided by the present disclosure will be more fully understood from the following description of exemplary embodiments when read together with the accompanying drawings, in which:

FIG. 1 shows an exemplary free fatty acid and complex compound containing fatty acids, e.g., esterified fatty acids.

FIG. 8 shows exemplary images of tissues samples. The samples were tested using the method and apparatus of the present disclosure. The fatty acid and total fatty acid content across the tissue was determined. In particular, FA 20:4, a marker of inflammation, can be identified and determined.

DETAILED DESCRIPTION OF THE INVENTION

Figure 2:
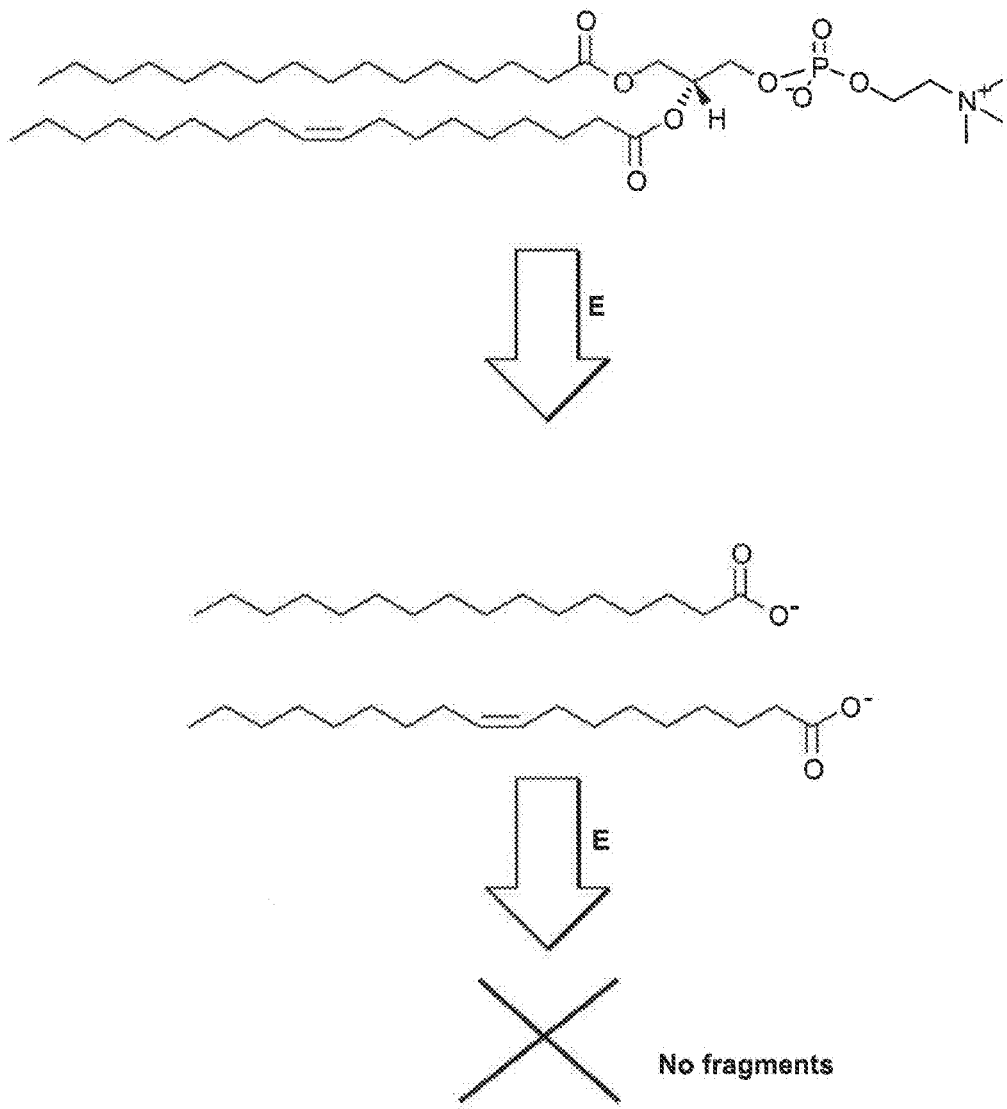
FIG. 2 shows an exemplary illustration of the methodology of the present disclosure. A complex compound containing fatty acids or a complex lipid can be tested at a low energy level wherein substantially no fragmentation occurs, e.g., 100° C., and at a higher energy level where fragmentation into free fatty acids occurs, e.g., 400° C. The free fatty acids are stable over a large range of high energy levels (e.g., they do not further fragment).
Figure 2:
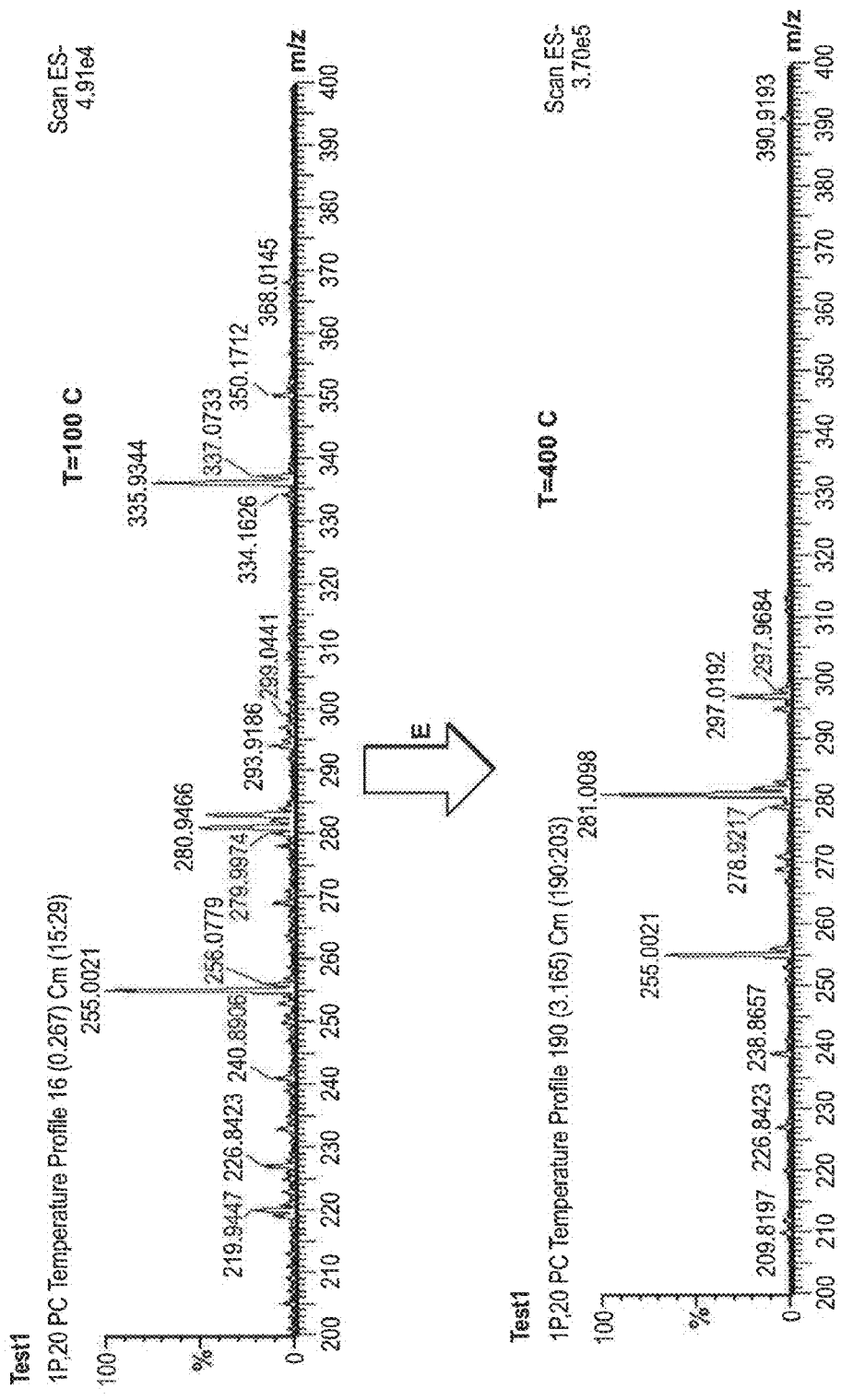
Figure 3:
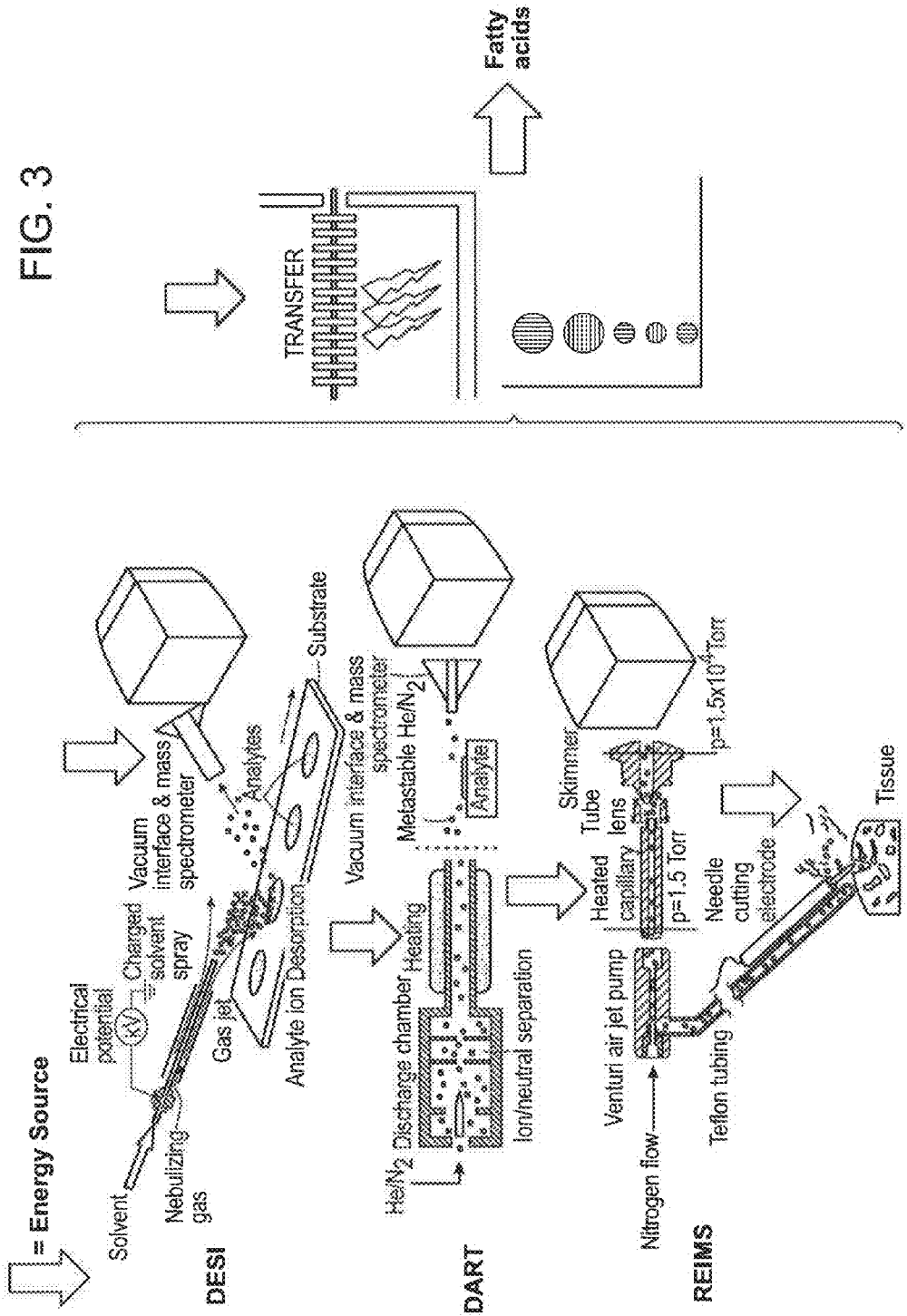
FIG. 3 shows three different embodiments of the present disclosure. Three different ionization sources, e.g., DESI, DART® and REIMS, are shown which can deliver energy at both low and high levels to induce fragmentation of complex compounds containing fatty adds prior to introduction into a mass spectrometer.
Figure 4:
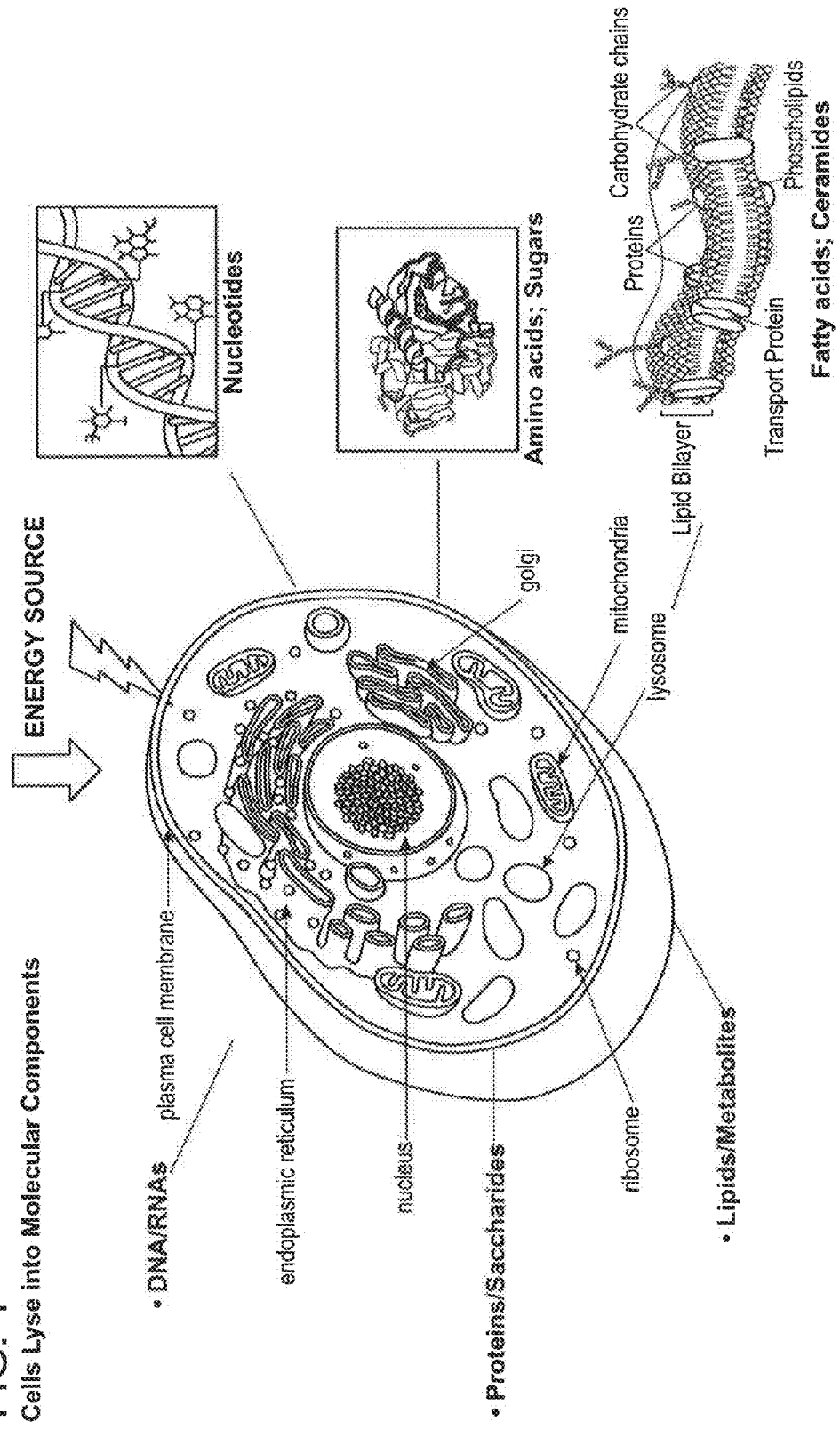
FIG. 4 shows an exemplary cell lyse that contains various molecular components which can have the fatty acid and total fatty acid content determined and identified using the method and apparatus of the present disclosure. The cell can contain DNA/RNA, protein/saccharides, lipids/metabolites, nucleotides, amino acids and sugar, fatty acids, ceramides, etc.
Figure 5:
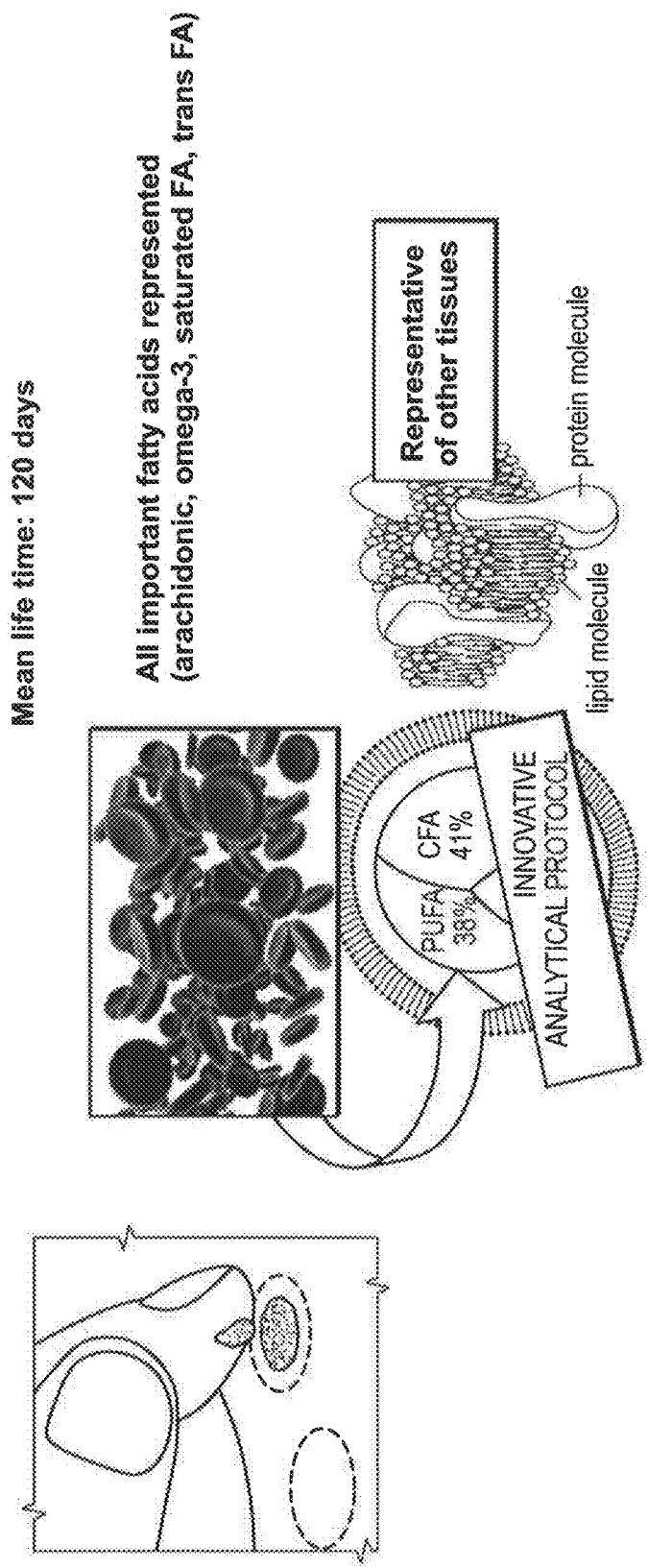
FIG. 5 shows an exemplary illustration of whole blood and red blood cells which can have the fatty acid and total fatty acid determined and identified using the method and apparatus of the present disclosure. The effect of diet, exercise, and other factors can also be evaluated by determining the total fatty acid content as contained in a sample, such as red blood cells. The average life of a blood cell is 120 days.

The present disclosure relates to methods and apparatus for the determination of free fatty acids and total fatty acids in a sample. In particular, the present disclosure relates to the determination of free fatty acids and total fatty acids using desorption ionization-mass spectrometry. The apparatus and method can include an ionization source capable of analyzing both free fatty acids and total fatty acids in a sample. The determination of free fatty acids and total fatty acids in a sample can have application in therapeutic, clinical and pharmaceutical applications.

In one embodiment, the present disclosure relates to a method of determining the total fatty acids in a sample including generating sample ions from a sample containing esterified and free fatty acids using a desorption ionization source, introducing the ions into a mass spectrometer, inducing fragmentation of the esterified fatty acids to free fatty acids before or after introduction into the mass spectrometer, and identifying the total fatty acids in the sample.

The "total fatty acids" in a sample is the sum of the free fatty acids and the fatty acids that are contained in complex compounds (e.g., esterified fatty acids), and can be fragmented and determined by the methods and apparatus of the present disclosure. Total fatty acids include esterified fatty acids, such as glycerolipids, glycerophospholipids, sterol lipids and sphingolipids.

The free fatty acids are those fatty acids not esterified, or otherwise contained in a complex compound. Free fatty acids include, for example, arachidonic acid, docosahexaenoic acid, eicosapentaenoic acid, linoleic acid, and alpha linoleic acid.

The sample can be any sample containing fatty acids contained in a complex compound, e.g., esterified fatty acids, that can be effectively tested using the surface desorption ionization-mass spectrometry methods and apparatus described herein. In one embodiment, the sample can be a diet, a food, a supplement, a dosage form or a biological sample. For example, the method and apparatus of the present disclosure can be used to determine the total fatty acid content in a biological sample, such as whole blood, plasma or red blood cells.

The sample can be analyzed with no substantial preparation, such as filtering, extraction, isolation or combinations thereof. The sample can be analyzed neat, or with no sample preparation. For example, a sample or samples can be swiped on glass capillaries and held, placed or otherwise introduced to the ionization source, e.g., held in a metastable gas beam between the direct analysis in real time ion source and a mass spectrometer detector. In one embodiment, the sample preparation is simple such that the sample can be a biological sample, e.g., a dried blood drop spotted on a slide or grid. The biological sample can also be blood in solution, as well as skin, sebum or saliva.

The sample can also be associated with a diet. The sample can be a food or foods, a supplement or supplements. The food or supplement(s) can be in any form, e.g., solid or liquid. The sample can also be associated with a dosage form to treat a condition. The dosage form can be in any form, e.g., tablet, capsule, pill, film, liquid, etc. Depending on the dosage form, the sample can be prepared by neat or by altering the dosage form to access the sample. The sample preparation can include removing a portion of the contents from inside the capsule.

The sample ions can be generated using any desorption ionization (DI) source or technique capable of effectively sampling the free fatty acids and compounds containing fatty acids (e.g., esterified fatty acids) from a sample for introduction into a mass spectrometer. The desorption ionization source or technique can also be any capable of real-time, rapid in-situ testing of solid or liquid samples. In one embodiment, the desorption ionization source is a surface desorption ionization source or technique.

In desorption ionization, the ionization process can begin by irradiating, or otherwise exposing, a defined spot on a sample, e.g., solid sample, using a focused energy source. The energy source can be an excitatory beam such as a laser, ions, or charged, solvent droplets. Upon impact, the sample's surface releases a vapor of ionized molecules that can be directed into a mass spectrometer. Alternatively, acoustic or thermal desorption can initiate the ionization process.

In one embodiment, the analysis of fatty acids using a surface desorption ionization-mass spectrometry system is provided. Fatty acids are particularly suited for surface desorption ionization because fatty acids can be in high abundance in biological and food samples, and they can ionize well in negative mode under DI conditions.

The surface desorption ionization source can operate by a technique selected from the group consisting of electrospray ionization, nano-electrospray ionization, matrix-assisted laser desorption ionization, atmospheric pressure chemical ionization, desorption electrospray ionization, atmospheric pressure dielectric barrier discharge ionization, atmospheric pressure low temperature plasma desorption ionization, laser-assisted electrospray ionization, and electrospray-assisted laser desorption ionization.

In particular, the surface desorption ionization source can operate by a technique selected from the group consisting of atmospheric solid analysis probe (i.e., ASAP), direct analysis in real time (DART®), rapid evaporative ionization mass spectrometry (REIMS), desorption electrospray ionization (DESI), matrix assisted laser desorption ionization (MALDI), laser-absorption electrospray ionization (LAESI), nanostructure and initiated mass spectrometry (NIMS).

The desorption ionization source can also be suitable or compatible with ambient mass spectrometry, e.g., a mass spectrometer operating at or near atmospheric pressure. In one embodiment, the desorption ionization source or technique is DART®, ASAP, REIMS or DESI. These ionization sources can be small and compatible with ambient mass spectrometry.

Direct Analysis in Real Time is an atmospheric pressure ion source that can instantaneously ionizes gases, liquids or solids in open air under ambient conditions, it is an ambient ionization technique that does not require sample preparation, so solid or liquid materials can be analyzed by mass spectrometry in their native state. Ionization can take place directly on the sample surface. Liquids can be analyzed by, for example, dipping an object (such as a glass rod) into the liquid sample and then presenting it to the DART® ion source. Vapors can be introduced directly into the DART® gas stream.

Atmospheric Solids Analysis Probe (ASAP) is an atmospheric pressure ion source that can directly analyze samples using an atmospheric pressure ionization (API) source. The ASAP probe can analyze solid, liquid, tissue, or material samples. In ASAP, vaporization of a sample can occur when it is exposed to a hot desolvation gas, e.g., nitrogen, from an probe, e.g., an electrospray ionization or atmospheric pressure chemical ionization probe.

Rapid Evaporative Ionization Mass Spectrometry (REIMS) is an ionization technique that can be used as a source for direct analysis of samples by mass spectrometry. REIMS is an atmospheric pressure ion source that can ionize gases, liquids or solids in open air under ambient conditions. The REIMS ionization source can be a probe that can be used to remotely test the samples. See U.S. Patent Publication No. 2012/0156712, the disclosure of which is incorporated herein in its entirety.

Desorption electrospray ionization (DESI) is an ambient ionization technique that can be used in mass spectrometry for chemical analysis. It is an atmospheric pressure ion source that ionizes gases, liquids and solids in open air under ambient conditions. DESI is a combination of electrospray (ESI) and desorption (DI) ionization methods. Ionization can take place by directing an electrically charged mist to a sample surface. The electrospray mist can be attracted to the surface by applying a voltage on the sample or sample holder. After ionization, the ions can travel through air into the atmospheric pressure interface which can be connected to a mass spectrometer.

Thermal desorption ionization can be used as the ionization mechanism. The sample, and biological components, can be exposed to different temperatures to induce ionization, See U.S. Patent Publication No. 2013/0299688 the disclosure of which is incorporated herein in its entirety.

The sample ions can be received or introduced to a mass spectrometer by any means or technique capable of effectively introducing ions into a mass spectrometer that can allow for the determination of free fatty acids and total fatty acids in a sample. For example, the ions can be introduced under ambient conditions.

The mass spectrometer can be any mass spectrometer capable of receiving the sample ions, of producing accurate mass measurements, and of identifying sample analytes of interest. Structural determination can be performed by the apparatus of the present disclosure by generating a first generation of ions during ionization, separating the ions, fragmenting the ions into a second generation of ions, separating the second generation of ions by ion mobility, and generating a third generation of ions for structural determination. See co-owned U.S. patent application Ser. No. 14/405,544, the disclosure of which is incorporated herein in its entirety.

The mass spectrometer can be a quadrupole mass spectrometer, portable ion trap mass spectrometer, time of flight mass spectrometer, Fourier transform ion cyclotron resonance mass spectrometry, orbi trap, or ion mobility spectrometer. For example, the mass spectrometer can be a single quadrupole detector, such as, for example a single quadrupole QDa® detector commercially available from Waters Technologies Corporation, Milford, Mass.

The analytes of interest can be analyzed by selection reaction monitoring in a quadrupole instrument. Selection reaction monitor involves pre-selection of a list of ion of interest or extracted from full scan accurate mass spectra, in which no ion is preselected but the quadrupole is scanned along all the mass range selected (e.g., 50-100 m/z). The mass range can include 40, 50, 60, 70, 80, 90, 100, 110, 120, 130, 140, 150, 160, 170, 180, 190, 200, 250, 300, 350, 400, 450, 500, 600, 700, 800, 900 or 1000 m/z. These values can define a ranges, such as about 50 to about 150 m/z.

The mass spectrometer can be operated in positive or negative mode. In one embodiment, the mass spectrometer is operated in negative mode under desorption ionization conditions. Fatty acids ionize particularly well in negative mode. The coupling of a mass spectrometer, e.g., a single quadrupole device, with desorption ionization can also allow for the direct analysis of fatty acids as a function of peak intensity or as a ratio between peaks or groups of peaks. The ratio of fatty acids can be used to normalize for variation in instrument settings and sampling. For example, a variation in intensity of one fatty acid(s) is compensated by an equivalent variation in another fatty acid(s). The ratio can normalize for difference between samples.

Inducing fragmentation of the complex compounds containing fatty acids, e.g., esterified fatty acids, to free fatty acids can be done before and/or after introduction into the mass spectrometer. For example, fragmentation can be induced by the ionization source, in the collision cell contained in the mass spectrometer, or both.

The present disclosure relates to a method of analyzing a sample at different ionization energy levels to determine free fatty acids and total fatty acids at a given ionization energy. The present disclosure relates to an apparatus and method of using various energy levels to analyze a sample. The total fatty acid values can be successively determined from a sample with ever increasing, or ramping, energy levels until the values of the total fatty acid levels off. In one embodiment, the ramping of the ionization energy during successive sampling can distinguish classes of fatty acids/lipids. For example, at a low temperature, e.g., 100° C., a portion or a majority of fatty acids can remain esterified. The classes can be distinguished by many features, including molecular weight. In another embodiment, esterified fatty acids can be isolated with ion mobility, post-desorption ionization.

In some embodiments, the energy or temperature of the ionization source may not be sufficiently high to efficiently ionize or fragment a representative sample. The complex components containing fatty acids, or that generate fatty acids upon fragmentation, may not all fragment at the same ionization energy. For example, the sample may contain fatty acids or a class of esterified fatty acids having different properties, such as different volatilities or fragmentation thresholds. There may be classes of complex components that undergo fragmentation to fatty acids only above a certain energy level. At a certain energy level or temperature, some fatty acids may be ionized, or fragmented and ionized, more readily than others, which can create a bias in the ratio at that energy level or temperature. In one embodiment, the present disclosure includes a step of determining a sufficient energy level (e.g., temperature in thermal desorption) to ionize a representative sample of all components. For example, the energy level can be tested at increasing values until the intensities or ratio of intensities for the analytes of interest stabilize at a constant value indicative of a representative sampling of analytes.

In one embodiment, the fragmentation is induced by the ionization source energy being sufficiently high to induce fragmentation of substantially all of the complex compounds containing fatty acids, e.g., esterified fatty acids, to free fatty acids.

The energy levels can be dependent on the ionization source. For example, a thermal desorption ionization source can deliver energy via temperatures from about 0° C. to about 750° C. The thermal desorption ionization source temperature can be greater than or less than about 50, 100, 150, 200, 250, 300, 350, 400, 450, 500, 550, 600, 650, 700 or about 50° C. These values can define a range, such as about 400 to about 550° C.

Fragmentation can also be induced in the collision cell contained in the mass spectrometer. In one embodiment, the fragmentation induced in a collision cell contained in the mass spectrometer is performed at a sufficiently high energy to induce fragmentation of substantially all of the esterified fatty acids to free fatty acids. For example, the collision energy (CE) can be greater than or less than about 1, 2, 3, 4, 5, 6, 7, 8, 9, 10, 15, 20, 25, 30, 35, 40, 45, 50, 55, 60, 65, 70 or about 75 V. These values can be used to define a range, such as about 6 to about 50 V. In general, the energy level of the ionization sources can be set or ramped from low to high settings, in which the low or minimal settings leave the molecules unaffected and the higher or maximal settings can generate complete fragmentation of one or more classes of macromolecules.

The apparatus can have an ionization source that can change the energy delivered. For example, the energy can be decreased to ionize free fatty acids in the sample. The energy can be decreased to a level that complex components containing fatty acids do not undergo fragmentation to generate fatty acids. The energy can also be increased to induce fragmentation of complex components containing fatty acids, or that generate fatty acids upon fragmentation. The total fatty acids, free and released/generated, can be ionized in the sample.

In an embodiment, the technology of the present disclosure includes a system that can adjust the energy from a lower setting to determine only free fatty acids, to a higher setting to induce fragmentation and determine the total fatty acid content, and vice versa. The time between the adjustment can be less than about 1 hour, 10 minutes, 5 minute, 1 minute, 10 seconds, 5 seconds, 1 second, 500 milliseconds, 100 milliseconds, 50 milliseconds, 10 milliseconds, 5 milliseconds, 1 millisecond, 0.5 milliseconds, and about 0.1 milliseconds. These values can also be used to define a range, such as from about milliseconds to about 0.1 milliseconds. In one embodiment, the same apparatus can be used to generate both analyses, to generate both the low and high energy values, or both.

For instance, a sample can be tested using a desorption ionization-mass spectrometry system capable of various energy settings. By increasing the ionization energy to induce fragmentation and introducing all of the fragmentations to the mass spectrometer, the absolute fatty acid (or fatty acyl) information can be collected. Fatty acyl groups can be detected as charged ions in negative mode [M-H]−. Post-acquisition analysis can differentiate the fatty acid (or fatty acyl) content and the distribution in various lipid classes according to the different biological samples analyzed. Fatty acid (or fatty acyl) composition can translate in molecular fingerprints of a tissue. Comprehensive screening and fingerprinting of fatty acid compositions for phenotype identification and comparative lipidomic analysis can be performed using the methodology and apparatus of the present disclosure. For example, red blood cells or other tissue biopsies can be analyzed using the present disclosure to assess a patient's nutritional status and disease risk.

The fatty acids and total fatty acids can be calculated from the mass spectrometry results. The amount (e.g., relative amount) can be calculated using the intensity of the peaks. The amount can be calculated with or without the use of an internal standard. The use of internal standards can provide semi-quantification after correcting for any isotopic contribution to the signal. For example, internal standards can be used to normalize the concentration of the fatty acids in the samples to obtain a more quantitative measurement. For example, the intensities of fatty acyl signals in negative mode can be proportional to their concentration and can be normalized as % of total fatty acids.

In general, the methods of the present technology are robust such that the sampling does not exhaust the components, analytes of interest or classes of analytes of interest, e.g., omega acids, in the sample. The ionization process can involve a short, e.g., less than about 10 seconds, 9, 8, 7, 6, 5, 4, 3, 2, 1, 0.5, 0.2 or about 0.1 seconds, exposure of the ionization source to the sample. These values can be used to define a range, such as between about 0.5 and about 2 seconds.

In general, the methods of the present disclosure can determine the fatty acids, the total fatty acid content, or both in a shorter time that methodology of the prior art. In some embodiments, the method can determine these within 10 minutes, 20, 30, 40, 50 or 60 minutes, or 1.5 hours, 2, 3, 4, 5, 6, 7, 8, 9, 10, 11, 12 or 24 hours as compared to traditional methodologies. These values can be used to define a range, such as between about 10 minutes and about 60 minutes. In another embodiment, the present disclosure can determine the fatty acids, the total fatty acid content, or both without sending a sample to a laboratory for analysis. The methodology can be used as a point of care test (e.g., doctor's office, pharmacy, etc.).

The present disclosure can determine the fatty acids, the total fatty acid content, or both without extraction, hydrolysis, filtration, derivatization, chromatographic separation (e.g., GC-FID) or combinations thereof. The prior art methodology involves one or more of these steps and can take hours to complete, e.g., at least about 2 hours. The method of the present disclosure can reduce the analysis time by about 10%, 20, 30, 40, 50, 60, 70, 80, 90, 100, 200, 300, 500, or about 1000% as compared to traditional methodologies. These values can be used to define a range, such as between about 20% and about 50%.

The present disclosure also relates to imaging. The fatty acid and total fatty acid values can be determined for a single point on a sample. Additional points of the sample can be tested to form an image of the sample showing the location of the fatty acids.

Figure 6:
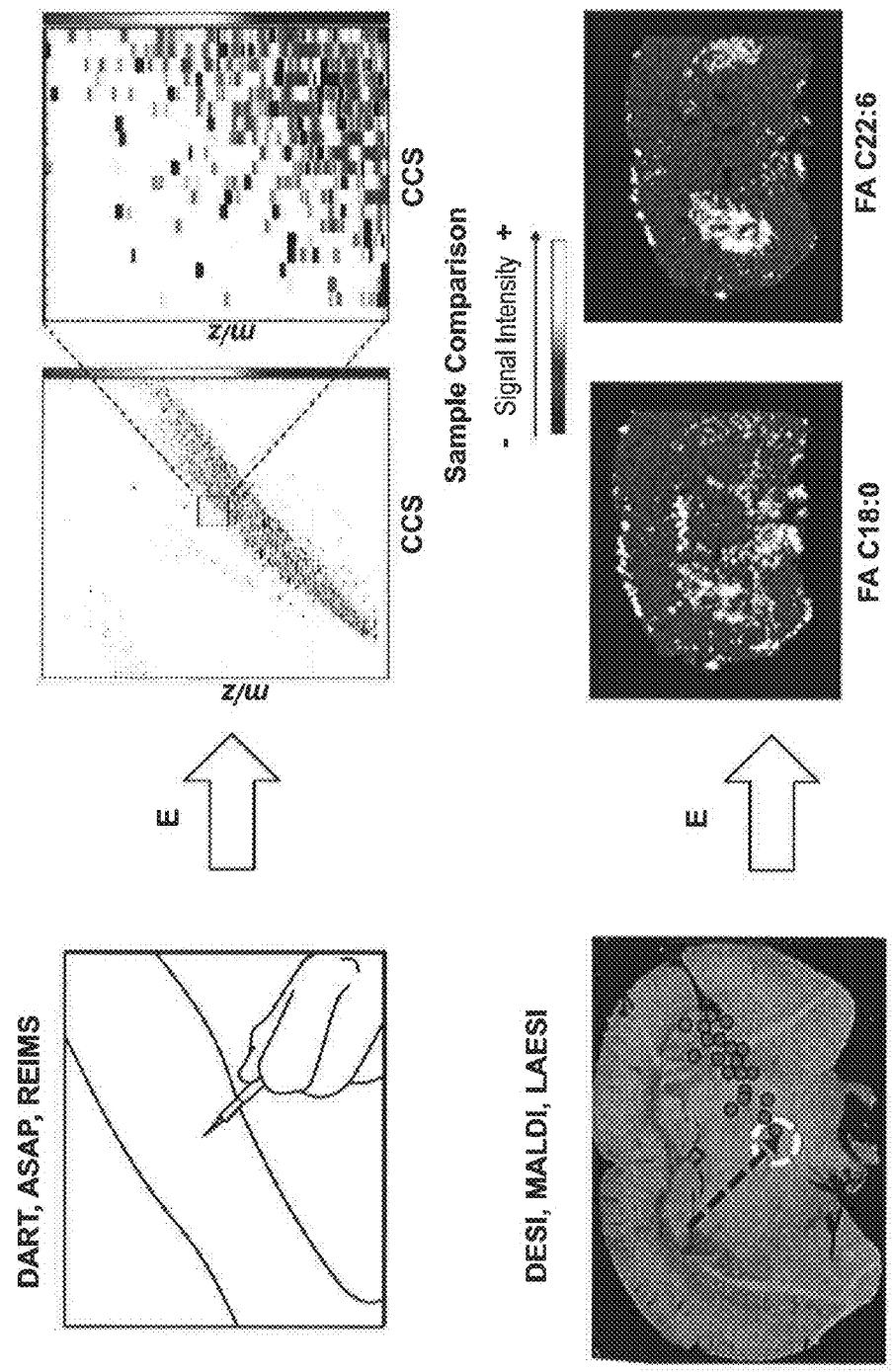
FIG. 6 shows two exemplary methodologies of the present disclosure, namely in situ analysis of fatty acids and total fatty acids in a sample, and fatty acid and total fatty acid imaging. In situ analysis can determine the amount and identity of fatty acids and total fatty acids in a sample. Imaging can provide a map showing locations of fatty acids and total fatty acids in a sample.
Figure 7:
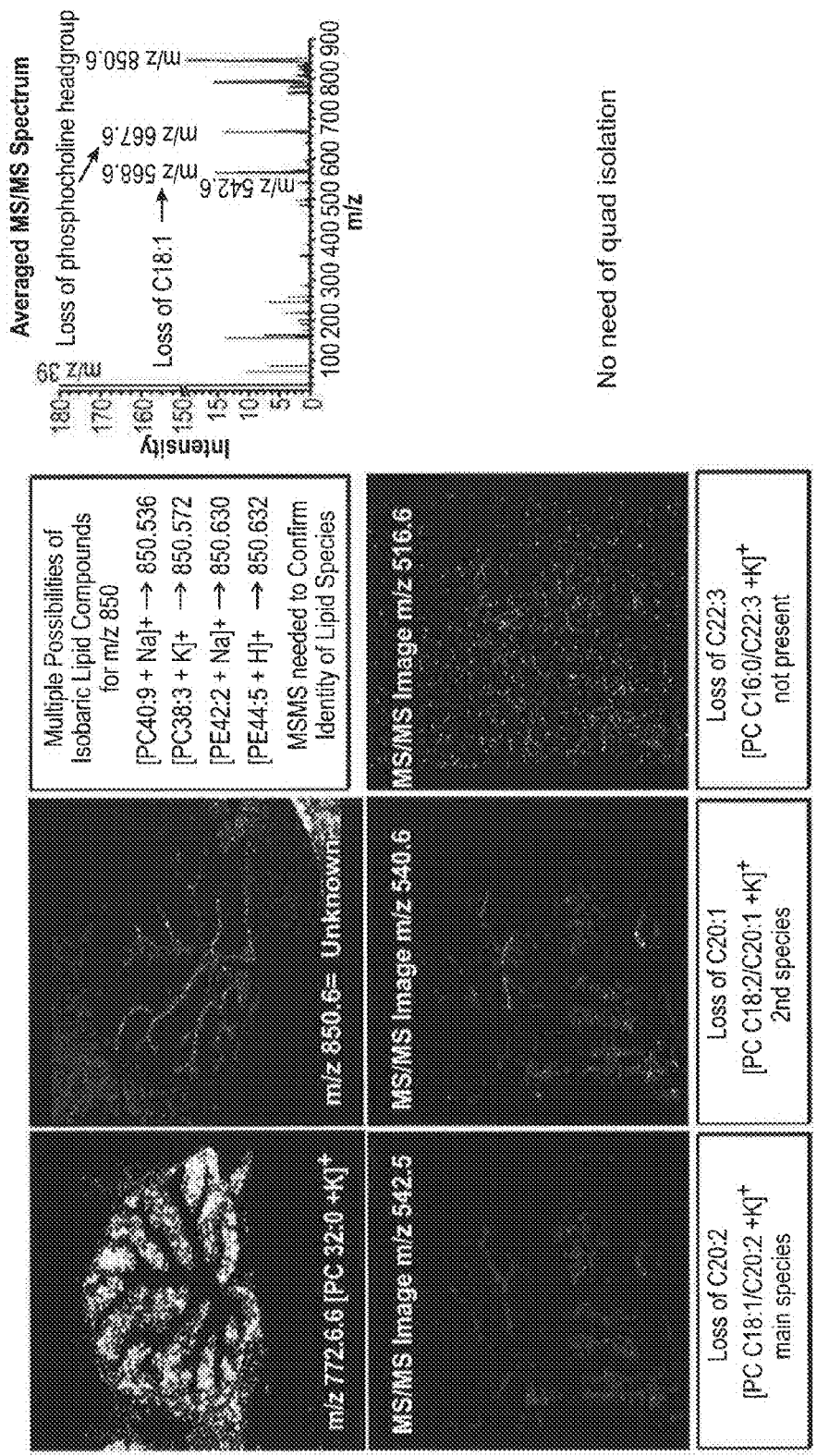
FIG. 7 shows exemplary images of the present disclosure showing the spatial distribution of fatty acids and total fatty acids in a sample. The loss of fatty acyl group(s) or the appearance of fatty acyl signals can be mapped across a sample. By increasing the ionization energy (e.g., excitation source energy, temperature) the composition of total fatty acid (e.g., free/unesterified fatty acids plus esterified fatty acids) content per pixel can be obtained. Alternatively, a post-ionization, "all fragmentation mode," or data-independent mode in a collision cell (e.g., cone, capillary or collision cell) before mass spectrometry detection can generate similar information by allowing for the analysis of total fatty acid composition.

In another embodiment, the present disclosure relates to a method of determining the spatial distribution of total fatty acids on a sample surface, e.g., imaging, including generating sample ions from a first location on a sample containing esterified fatty acids and free fatty acids using an ionizing source, introducing the ions into a mass spectrometer, inducing fragmentation of the esterified fatty acids to free fatty acids before or after introduction into the mass spectrometer, determining the total fatty acids in the sample at the first location, and repeating these steps on a plurality of locations. FIGS. 6-8 show example images of tissue samples having fatty acids mapped across the tissue. The various fatty acids can be determined as free fatty acids or can be determined as total fatty acids when analyzed under high energy conditions.

The first location on a sample surface can be any location. The additional locations on the sample surface, e.g., the plurality of locations, can be any other locations on the sample surface. In one embodiment, the locations are all separate locations on the sample surface. The analysis at each location can be performed by either direct sampling from the sample surface by the desorption ionization source, or from samples removed from the plurality of locations.

The distance between adjacent locations can vary based on the level of detail and resolution desired for the spatial distribution analysis. To provide sufficiently detailed spatial distribution analysis, the average distance between adjacent locations can be less than about 100 mm, 50, 10, 1, 0.5, 0.01, 0.005 or about 0.001 mm. These values can also be used to define a range, such as between about 1 and 0.001 mm.

The technology of the present disclosure can be used to determine the free fatty acid and total fatty acid from whole blood, plasma, red blood cells, and other samples. In some embodiments, the sample matrix does not substantially interfere with the analysis. In particular, the determination of free fatty acids and total fatty acids can be performed on red blood cells. Because the average life of a red blood cell is about 120 days, red blood cell analysis can be informative of the fatty acid profile of a subject over a relatively longer period (e.g., weeks or months). Red blood cells are less prone to changes in diet and intake of fatty acids. Other samples may be more or less prone to changes over time. For example, urine samples may be more prone to hourly or daily changes based on the immediate diet, food, drinking habits, etc. Brain tissue samples may be less prone to hourly, daily, weekly, etc. changes.

The analysis of total fatty acids from red blood cells can have many advantages over the other potential sources including (i) the lipid bilayer can be more reflective of tissue fatty acid levels than serum fatty acids, (ii) red blood cell fatty acids have a half-life that is 4-6 times longer than serum fatty acids, which can better reflect long-term conditions, (iii) the fatty acids levels in red blood cells are not significantly influenced by fed or fasting states, (iv) the fatty acids levels in red blood cells are responsive to increasing intakes, (v) red blood cell composition is less influenced by dyslipidemias than serum fatty acids, (vi) the fatty acids in red blood cells are less variable than their levels in serum, (vii) laboratory assessment of fatty acids levels in red blood cells is simpler than in lipoprotein or lipid fraction fatty acids, and (viii) the red blood cells are resilient to variations in pre-analytical storage conditions.

The method of the present disclosure can be applied to red blood cells and other blood components (e.g., plasma, serum, lymphocytes) or tissue biopsies, sebum and biofluids. The method can also be applied to all molecular components of cells, such as sugars, nucleotides and amino acids deriving from oligosaccharides, oligonucleotides and peptides/proteins respectively. The method can be applied both to liquid and solid samples of both biological origin and food. Chemical substructures could also be identified a series of fragment ions that may be found physiologically as neutral molecular species. For example, fragments generated by the high energy desorption ionization analysis of complex lipid species are also common products of enzymatic hydrolysis (e.g., lysophospholipids and fatty acids) or chemical rearrangement (e.g., products of intramolecular cyclization of phosphate groups).

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

The fatty acid and total fatty acid content in brain tissues was determined using desorption ionization-mass spectrometry. The apparatus used consisted of a surface desorption ionization, e.g., direct analysis in real time (DART®, Ion-Sense, MA, USA), coupled to a single quadrupole mass spectrometer, e.g., Acquity® QDa®, Waters Corporation, Milford, Mass., USA. The acquisition time was about 5-10 seconds, ionization DART®+ve and −ve; Cone voltage 20.0 V; Source temp. 120.0° C.; DART® temp. 50 to 450° C.

The overall percent of omega-3 DHA in various brain regions was determined by the application of high energy fragmentation post DI and monitoring the m/z relative to the loss of the DHA acyl group (m/z 327.3) in negative mode. An image of the distribution of the omega-3 DHA can be constructed from the results. Other fatty acids were also monitored and their content determined in post acquisition.

What is claimed is:

1. A method of determining the total fatty acids and free fatty acids in a sample comprising:
   (i) generating sample ions from a sample containing esterified and free fatty acids using a desorption ionization source;
   (ii) introducing the ions into a mass spectrometer;
   (iii) inducing fragmentation of the esterified fatty acids to free fatty acids before or after introduction into the mass spectrometer; and
   (iv) identifying, simultaneously, the total fatty acids and the free fatty acids in the sample.

2. The method of claim 1 wherein the esterified fatty acids comprise glycerolipids, glycerophospholipids, sterol lipids or sphingolipids, or combinations thereof.

3. The method of claim 1 wherein the desorption ionization source operates by a technique selected from the group consisting of electrospray ionization, nano-electrospray ionization, matrix-assisted laser desorption ionization, atmospheric pressure chemical ionization, desorption electrospray ionization, atmospheric pressure dielectric barrier discharge ionization, atmospheric pressure low temperature plasma desorption ionization, laser-assisted electrospray ionization, and electrospray-assisted laser desorption ionization.

4. The method of claim 1 wherein the desorption ionization source operates by a technique selected from the group consisting of atmospheric solid analysis probe, direct analysis in real time, rapid evaporative ionization mass spectrometry, desorption electrospray ionization, matrix assisted laser desorption ionization or nanostructure and initiated mass spectrometry.

5. The method of claim 1 wherein the mass spectrometer is a quadrupole mass spectrometer, portable ion trap mass spectrometer, time of flight mass spectrometer, Fourier transform ion cyclotron resonance mass spectrometry, orbi trap or ion mobility spectrometer.

6. The method of claim 1 wherein the mass spectrometer is operated in negative ionization mode.

7. The method of claim 1 wherein fragmentation is induced by the ionization source energy being sufficiently high to induce fragmentation of substantially all of the esterified fatty acids to free fatty acids.

8. The method of claim 1 wherein fragmentation is induced in a collision cell contained in the mass spectrometer, wherein the energy in the collision cell is sufficiently high to induce fragmentation of substantially all of the esterified fatty acids to free fatty acids.

9. The method of claim 1 wherein the sample is a biological sample.

10. The method of claim 1 wherein steps (i)-(iv) are performed in less than 24 hours.

11. The method of claim 1 wherein the free fatty acids comprise arachidonic acid, docosahexaenoic acid, eicosapentaenoic acid, linoleic acid, or alpha linoleic acid, or combinations thereof.

12. A method of determining the spatial distribution of total fatty acids and free fatty acids on a sample surface comprising:
  (i) generating sample ions from a first location on a sample containing esterified fatty acids and free fatty acids using an ionizing source;
  (ii) introducing the ions into a mass spectrometer;
  (iii) inducing fragmentation of the esterified fatty acids to free fatty acids before or after introduction into the mass spectrometer;
  (iv) determining, simultaneously, the total fatty acids and the free fatty acids in the sample at the first location, and
  (v) repeating (i)-(iv) on a plurality of locations.

* * * * *